United States Patent [19]
Hammond

[11] 3,976,655
[45] Aug. 24, 1976

[54] METHOD OF MAKING 2,6-BIS(METHYLAMINO) OR 2,6-BIS(DIMETHYLAMINO)PYRIDINES

[75] Inventor: Peter R. Hammond, Livermore, Calif.

[73] Assignee: The United States of America as represented by the Secretary of the Navy, Washington, D.C.

[22] Filed: June 20, 1975

[21] Appl. No.: 589,489

[52] U.S. Cl. .................... 260/296 R; 260/294.8 E; 260/294.8 F; 260/294.9; 260/295 R; 260/295.5 R; 331/94.5 L
[51] Int. Cl.² ........................................ C07D 213/74
[58] Field of Search ..................... 260/296 R, 585 A

[56] References Cited
OTHER PUBLICATIONS

Klingsberg "Pyridine and Its Derivatives" part 2 (1961), pp. 352–353.

Houben-Weil "Met. der Org. Chemie" vol. 11/1 (1957), p. 32.

Sidgwick "The Chemistry of Nitrogen" p. 528 (1956).

*Primary Examiner*—Henry R. Jiles
*Assistant Examiner*—R. W. Ramsuer
*Attorney, Agent, or Firm*—R. S. Sciascia; Roy Miller; David J. Aston

[57] ABSTRACT

Methods for preparing 2,6-bis(dimethylamino)pyridine and 2,6-bis(methylamino)pyridine are disclosed. The methods involve the reaction of 2,6-dichloropyridine with an aqueous solution of either dimethylamine or methylamine, in the presence of copper sulfate for 15 hours in a bomb at 160°C. The compounds synthesized are useful as lasing dyes.

2 Claims, No Drawings

METHOD OF MAKING 2,6-BIS(METHYLAMINO) OR 2,6-BIS(DIMETHYLAMINO)PYRIDINES

BACKGROUND OF THE INVENTION

1. Field of the Invention.

This invention relates to the synthesis of 2,6-bis(-dimethylamino)pyridine, 2,6-bis(methylamino)pyridine, to their use as lasing dyes and, more generally, to the use of other similar compounds as lasing dyes.

2. Description of the Prior Art.

It is a well known fact that certain dyes will lase. At the present time, there is a considerable amount of research going on in efforts to find stable dyes which will lase in the ultraviolet region of the spectrum. Dyes with the ability to lase in the ultraviolet are useful in processes being developed for the separation of isotopes. Dyes which will lase in the ultraviolet are, however, rare and, to the best of the inventor's knowledge, it has not been previously known that the dyes disclosed herein will lase in the ultraviolet region.

2,6-Bis(methylamino)pyridine, one of the dyes whose preparation is disclosed herein, has been prepared before. Its preparation was described by Bernstein, Stearns, Shaw and Lott in the *Journal of the American Chemical Society*, Vol. 69, pages 1151–1158 (1947). Bernstein et al prepared the compound by reacting 2,6-dibromopyridine with an aqueous solution of methylamine for 8 hours in a bomb at 190°C. Bernstein et al obtained a 59% yield and disclosed the compound to have some antiparasitic activity when tested against *P. Lophurae* in ducklings.

No preparation of 2,6-bis(dimethylamino)pyridine (the other dye whose preparation is disclosed herein) is, insofar as is known by the inventor, given in the literature. A search of *Chemical Abstracts* revealed the use of 2,6-bis(dimethylamine)pyridine as a starting compound in the synthesis of perchlorinated cyano compounds (U.S. Pat. No. 3,711,480) but failed to reveal any synthesis for the compound. That is, U.S. Pat. No. 3,711,480, while it discloses the use of 2,6-bis(dimethylamino)pyridine, does not disclose a preparation for it and the inventor could not find a preparation disclosed elsewhere.

SUMMARY OF THE INVENTION

An improved method for preparing 2,6-bis(methylamino)pyridine and a method for preparing 2,6-bis(dimethylamino)pyridine have now been found. The methods involve reacting aqueous solutions of methylamine [in the case of the preparation of 2,6-bis(methylamino)pyridine] or dimethylamine [in the preparation of 2,6-bis(dimethylamino)pyridine] with 2,6-dichloropyridine in the presence of copper sulfate catalyst in a bomb for 15 hours at 160°C. The method in which 2,6-bis(methylamino)pyridine is prepared gives a 71% yield as compared with the 59% yield disclosed by Bernstein et al. When either of the compounds are dissolved in either water or alcohol and hydrochloric or perchloric acid and placed in a suitable laser cavity, the compounds will lase in the ultraviolet.

DESCRIPTION OF THE PREFERRED EMBODIMENT

The preferred embodiment of this invention may conveniently be described by a series of specific examples.

EXAMPLE 1

Preparation of 2,6-bis(methylamino)pyridine.

2,6-Dichloropyridine (5.0g), copper sulfate (1.0g), and a 40% aqueous methylamine solution (40ml) were placed in a steel bomb. The reaction mixture was then heated for 15 hours at a temperature of 160°C. Upon completion of the reaction period, the mixture was cooled and extracted with 5x100ml of ether. The extract was dried over sodium sulfate and dried to a light brown gum. The gum crystallized on standing. A 71% yield (3.3g) of the crystals was obtained. The crystals had a nuclear magnetic resonance (NMR) spectrum in accord with the proposed structure:

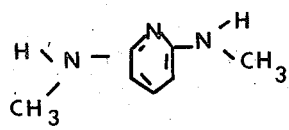

and could be recrystallized from n-hexane. The melting point of the crystals was 73.5° – 74.0°C.

Anal. Calcd. for $C_7H_{11}N_3$: C, 61.3; H, 8.03; N, 30.66. Found: C, 61.2; H, 7.96; N, 30.57.

EXAMPLE 2

Preparation of 2,6-bis(dimethylamino)pyridine.

2,6-Dichloropyridine (5.0g), copper sulfate (1.0g) and 40% aqueous dimethylamine solution (40ml) were placed in a steel bomb and heated at 160°C for 15 hours. Upon completion of the reaction (heating) period, the mixture was cooled and extracted with ether. The extract was dried over sodium sulfate and evaporated. The residue (after evaporation of the ether) was extracted three times with hot pentane, filtered and evaporated. A light brown mobile oil which crystallized on standing was obtained. A 78% yield (4.4g) of the crystals were obtained. The NMR spectrum of the crystals agreed with the proposed structure of 2,6-bis(-dimethylamino)pyridine:

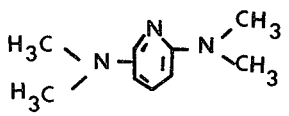

The total sample was headed with water (250ml), 70% perchloric acid (5ml) and decolorizing charcoal (1g) for 10 minutes, filtered and allowed to cool to deposit pale cream plates of the pyridinium perchlorate, m.p. 207°–208°C. Anal. Calcd. for $C_9H_{16}N_3ClO_4$: C, 40.7; H, 6.03; N, 15.83; Cl, 13.4. Found: C, 40.92; H, 6.12; N, 15.92; Cl, 13.19.

EXAMPLE 3

$5 \times 10^{-3}$ Molar solutions of (1) 2,6-diaminopyridine, (2) 2,6-bis(methylamino)pyridine and (3) 2,6-bis(-dimethylamino)pyridine in either water or alcohol which had been acidified to 0.1N with either hydrochloric acid or perchloric acid were made up. The solutions were placed, one by one, in the cuvette of an Avco-Everett, C400 nitrogen laser — "Dial-a-line" dye laser combination and pumped. The dyes lased readily up to the 100Hz pulse rate.

The chloride and perchlorate salts of 2,6-diaminopyridine, 2,6-bis(methylamino)pyridine and 2,6-bis(dimethylamino)pyridine may be said to be members of a general class of salts having structures which may be represented by the general structure:

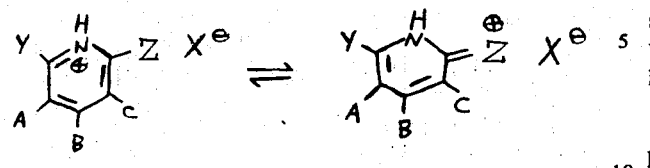

wherein Y is $NR_1R_2$ and R, $R_1$ and $R_2$ are selected from the group consisting of H, alkyl and aryl or wherein Y an amino radical contained as part of one or more heterocyclic groups having 5 to 6 atoms in the heterocyclic nucleus; wherein $Z^+$ is $NR_3^+R_4$ and $R_3$ and $R_4$ are selected from the group consisting of H, alkyl, and aryl or wherein $Z^+$ is an amino radical contained as part of one or more heterocyclic groups having 5 to 6 atoms in the heterocyclic nucleus; wherein one or more of the groups A, B and C may be a common substituent of pyridine derivatives such as H, alkyl, aryl, alkaryl, aralkyl, halogenated alkyl such as trifluoromethyl, halogenated aryl, aryl sulfonyl, sulfonamide, cyano, alkoxy, COOH or an ester radical; and wherein $X^-$ is a non-reducing and non-oxidizing anion such as $Cl^-$ or $ClO_4^-$. Since the dyes of Example 3 lase, it is reasonable to assume that other members of the general class represented by the foregoing structure will lase also if and when they are ever prepared. (Some have been prepared and some have not.)

What is claimed is:

1. A method for preparing 2,6-bis(dimethylamino)-pyridine comprising the steps of:
   A. preparing a reaction mixture containing 2,6-dichloropyridine, aqueous dimethylamine and copper sulfate;
   B. confining said reaction mixture in a bomb; and
   C. heating said confined reaction mixture at a temperature of 160°C for 15 hours.

2. A method for preparing 2,6-bis(methylamino)-pyridine comprising the steps of:
   A. preparing a reaction mixture containing 2,6-dichloropyridine, aqueous methylamine and copper sulfate;
   B. confining said reaction mixture in a bomb; and
   C. heating said confined reaction mixture at a temperature of 160°C for 15 hours.

* * * * *